US009470643B2

(12) United States Patent
Stauber

(10) Patent No.: US 9,470,643 B2
(45) Date of Patent: Oct. 18, 2016

(54) ATTACHMENT FOR IMPROVING THE RECEPTION QUALITY OF A MATERIAL DETECTOR DEVICE

(71) Applicant: AMPASS-EXPLORER Corp., Tortola (VG)

(72) Inventor: Siegfried Stauber, Zurich (CH)

(73) Assignee: AMPASS-EXPLORER Corp., Tortola (VG)

( * ) Notice: Subject to any disclaimer, the term of this patent is extended or adjusted under 35 U.S.C. 154(b) by 712 days.

(21) Appl. No.: 13/957,507

(22) Filed: Aug. 2, 2013

(65) Prior Publication Data

US 2014/0035556 A1    Feb. 6, 2014

(30) Foreign Application Priority Data

Aug. 6, 2012   (EP) .................................... 12401164

(51) Int. Cl.
| | |
|---|---|
| *H01Q 1/24* | (2006.01) |
| *G01N 27/00* | (2006.01) |
| *G01V 3/12* | (2006.01) |
| *G01D 11/30* | (2006.01) |

(52) U.S. Cl.
CPC ................. *G01N 27/00* (2013.01); *G01V 3/12* (2013.01); *G01D 11/30* (2013.01)

(58) Field of Classification Search
USPC ....................... 324/207.2, 71.1; 343/702, 718
See application file for complete search history.

(56) References Cited

U.S. PATENT DOCUMENTS

| 2005/0028890 A1 | 2/2005 | Sakaki et al. |
| 2009/0033315 A1* | 2/2009 | Kawashima ........... G01D 5/145 324/207.2 |
| 2011/0248705 A1 | 10/2011 | Matsumoto et al. |

FOREIGN PATENT DOCUMENTS

| CH | 696 893 A5 | 1/2008 |
| CH | 700 278 B1 | 6/2010 |
| DE | 10 2011 006 488 A1 | 10/2011 |
| EP | 0 984 460 A2 | 3/2000 |
| WO | WO 2007/064271 A | 6/2007 |

* cited by examiner

*Primary Examiner* — Minh Phan
(74) *Attorney, Agent, or Firm* — Renner, Otto, Boisselle & Sklar, LLP

(57) ABSTRACT

An attachment for a material detector device having a search antenna polarization instrument, where the material detector device has a housing with an antenna surface assigned to a detection direction, having magnets positioned opposite each other with like poles facing each other whose pole surfaces are covered by a tinned copper or oxidized aluminum layer, where the magnets and the copper or aluminum layer have at least one through bore and the magnets can be or are positioned on the housing of the material detector device extending perpendicular to the antenna surface and form a magnetic field space between the magnets in front of the antenna surface, as well as a material detector device having a rectangular housing with such an attachment for improving the reception quality. The result of this attachment is that the acoustic signals which indicate presence or absence are separated from each other more sharply.

14 Claims, 4 Drawing Sheets

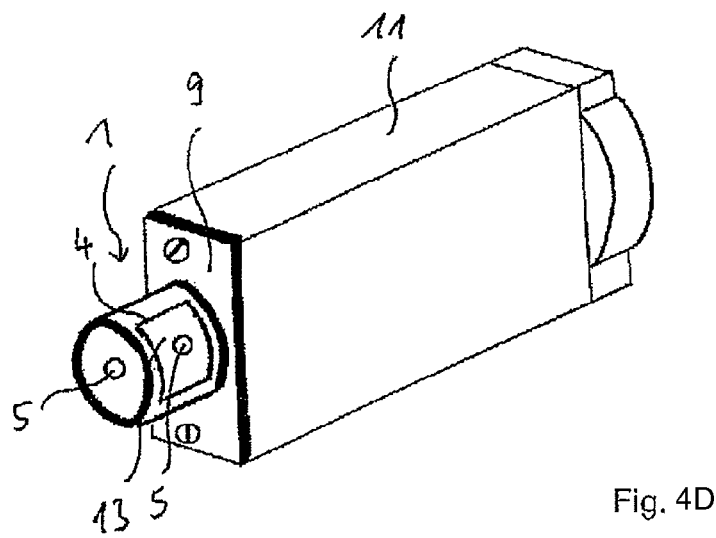
Fig. 4D
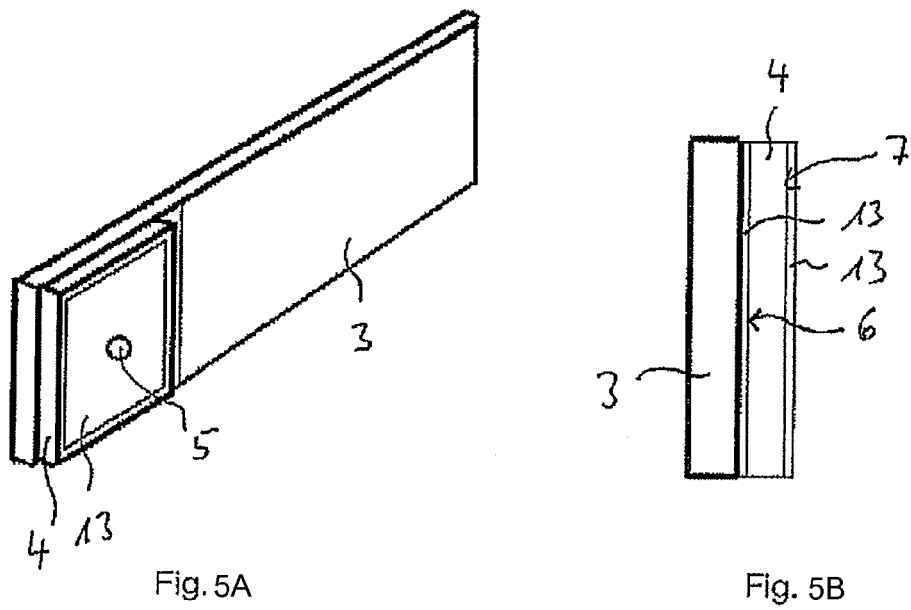
Fig. 5A
Fig. 5B

ATTACHMENT FOR IMPROVING THE RECEPTION QUALITY OF A MATERIAL DETECTOR DEVICE

CROSS-REFERENCE TO RELATED APPLICATION

The present application claims priority under 35 USC §119 to European Patent Application No. 12 401 164.4, filed Aug. 6, 2012, the entire disclosure of which is incorporated herein by reference.

TECHNICAL FIELD OF THE INVENTION

The present invention relates to an attachment for a material detector device having a search antenna polarization instrument, the material detector device having a housing with an antenna surface assigned to a detection direction.

DESCRIPTION OF THE RELATED ART

Such a material detector device is known from CH 696 893 A5. These devices are suitable for locating sought objects over relatively large distances by means of an antenna matchable to the particular material. This material detector device normally has a housing in which an appropriate search antenna polarization instrument is situated. The housing itself has an antenna surface through which the necessary signal for locating the sought object is transmitted and the reflection signal is received. Such a housing is disclosed in CH 700 278 B1.

It has been found in practice that the measurements are strongly influenced by environmental influences on the signal.

The object of the present invention is therefore to propose a possibility whereby the precision of such a material detector device can be improved.

This object is fulfilled according to the invention using the features described herein. According to the invention an attachment or a material detector device having an attachment is provided, the attachment having two magnets with like poles facing each other, whose pole faces are covered by a tinned copper or oxidized aluminum layer, the magnets and the copper or aluminum layer having at least one through bore and the magnets being positionable or positioned on the housing of the material detector device extending perpendicular to the antenna surface, so that a magnetic field space located in front of the antenna surface forms between the magnets. The copper or aluminum layer can be shaped as a foil or film, where the coating of tin or oxide may be in the p range. As is known, after aluminum has been stored in the air a thin, spontaneous layer of aluminum oxide results. However, an electrolytically applied aluminum oxide layer (anodized aluminum) can also be used. Both possibilities are meant by the term "oxidized aluminum."

Surprisingly, it has been found that the reception quality of the material detector device is improved substantially by an attachment of such a design, since the influence of interference on the measuring beam of the material detector device is eliminated. The function of improvement to the reception quality presumably consists in ions in the air (oxygen and nitrogen cations) that accompany the main beam non-directionally and at various velocities being forced into a magnetic orbit around the hole before the housing with the receiving antenna and slowed down by eddy currents. Depending on the polarity of the magnets, these are cations (south pole-south pole) or anions (north pole-north pole). The tin applied to the copper causes tin oxide to form. Through the amphoteric catalyst effect, this brings about a recombination of the ions to $O_2$ or $N_2$. The recombination is intensified if aluminum oxidized on both sides is used instead of tinned copper. Aluminum oxide is also suitable for the recombination.

SUMMARY OF THE INVENTION

According to a preferred design, the measuring quality of the measurement signal, and thus the precision of measurement of the material detector device, becomes significantly more exact if the copper or aluminum layer perpendicular to the antenna surface is at least 15.5 mm wide.

An additional improvement then appears if the magnets have at least one through bore, which by particular preference is centered in the magnetic field space. The arrangement of such magnets at the specified location brings about fewer interference effects on the measurement and produces sharper acoustic signals, which favor precise location of the sought object more rapidly.

The attachment for improving the reception quality can advantageously have a magnet holder, which consists of a retaining plate that extends perpendicular to the antenna surface, is made of a non-magnetizable material, and accommodates the magnet outside and/or inside on at least one free end. According to another design, the magnet holder can be formed as a pipe, which likewise extends perpendicular to the antenna surface and is made of a non-magnetizable material. Here too, the magnets can be attached outside and/or inside. Since standard commercial magnets are surrounded with a plastic material (so-called plastic ferrite), which has a dimension that is greater than the lateral delimitation of the magnetic field space by the magnets at least requires, the plastic ferrite can be stuck laterally to the housing of the material detector device correspondingly simply, or attached separably by means of a Velcro strip, and thus extend with the area of the magnets effective for the desired application, to the side of the antenna surface and perpendicular to it. Depending on the construction, the magnet holder can have a holding element which on the one hand carries the magnet holder and on the other hand is suitable for affixing the magnet holder separably to the housing. Thus the holder can be attached quickly to the relevant apparatus when measuring, and can be detached just as quickly if the placement of such a zone in front of the antenna surface is not necessary for other measurements. With the tubular version, a quadrupole magnet arrangement can also be chosen.

The attachment according to the invention can be secured firmly to the material detector device in such a way that the magnet holder is secured firmly to the wall of the housing that forms the antenna surface, or directly to the magnets, to the side, as described above. The securing can be accomplished for example by sticking the magnet holder to the side wall of the housing that has the antenna surface, or by attaching it to a wall that forms the side wall of the housing.

The separable securing of the magnet holder to the housing is done advantageously using a holding element, which has appropriately suitable separable fixing means, which engage with corresponding devices on the housing and can be released either by hand or by means of a tool to separate them. It is also possible to position the magnet holders on the walls of the housing which extend perpendicular to the antenna surface. To this end, the magnet holder advantageously has retaining plates, which are attached to these walls by gluing as a fixed connection or by screws or Velcro strips as a separable connection, and thus extend to the side of the antenna surface and perpendicular to it.

Additional features of the invention derive from the following description of the exemplary embodiments, in combination with the claims and the accompanying drawing. The individual features can be realized individually or in groups for embodiments of the invention. The figures depict the following:

DETAILED DESCRIPTION OF THE INVENTION

Figure 1:
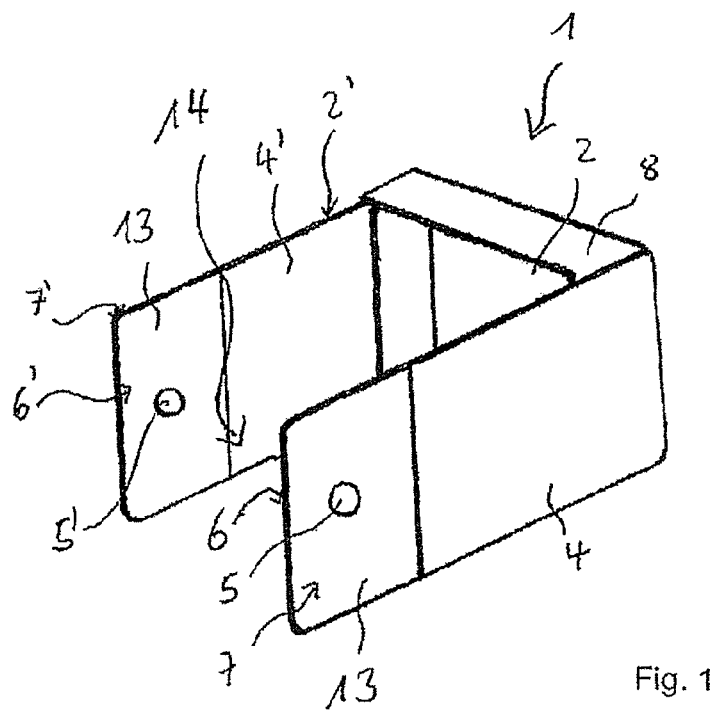
FIG. 1 a perspective view of an attachment according to the invention for improving the reception quality, to be secured separably to a corresponding housing with lateral magnet holders.

FIG. 1 shows an exemplary embodiment with an attachment 1 for improving the reception quality, having two elongated plastic magnets 4, 4', which have a stuck-on tinned copper foil 13 on their free ends on a width of 15.5 mm, both on the south pole side 6, 6' and on the north pole side 7, 7'. The size of the plastic magnets 4, 4' is usually 58×31 or 31×15.5 mm, depending on the application. The magnets 4, 4' face each other with their south pole sides 6, 6', on which the copper foil 13 is located, and have a through bore 5, 5' which leads from the inner copper foil 13 of the south pole side 6, 6' to the outer copper foil 13 of the north pole side 7, 7'. At the other end, the magnets 4, 4' are connected via a holding element 8, by means of which the entire attachment 1 is securable on a housing 10 (see FIG. 4a). In this case the elongated magnets 4, 4' themselves serve as a magnet holder 2, 2', because the effective zone is in the area of the copper foil 13 with the magnetic field space 14 between the magnet holders 2, 2'. Instead of the elongated magnets 4, 4', according to FIG. 5 it is also possible in each case to use a retaining plate 3 as magnet holder 2, which has a magnet 4, 4' with the relevant copper foil 13 only at its free end. The magnets 4, 4' with the copper foil 13 are stuck with their south pole side 6, 6' on the outside of the relevant retaining plate 3. FIGS. 5a and 5b show only a retaining plate 3 with magnet 4; corresponding to this there is a retaining plate (not shown) for the other side, similar to that in FIG. 1. The retaining plate 3 is made of a non-magnetizable material, such as aluminum or chromium steel. The diameter of the bores is 3 to 5 mm, and the magnetic field strength of the magnets is 10 mT±2 mT.

Figure 2:
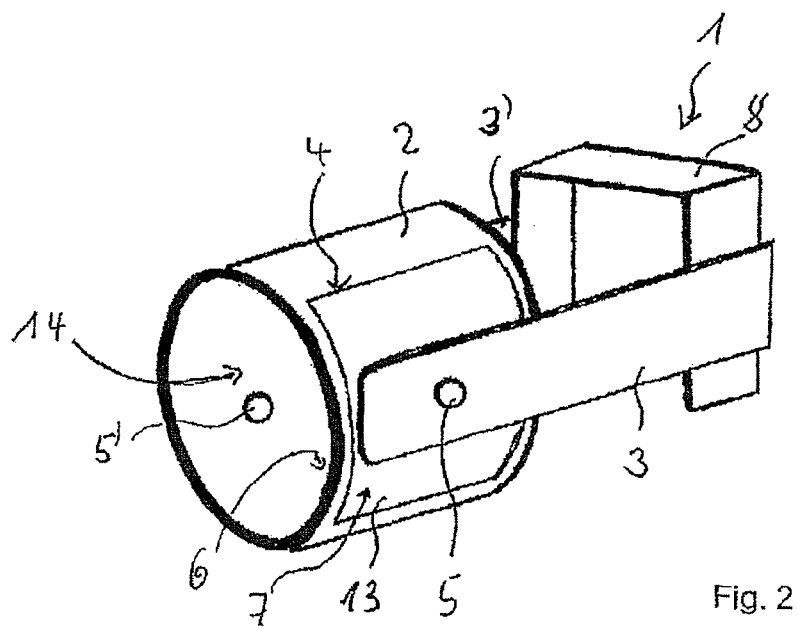
FIG. 2 a perspective view of an attachment according to the invention for improving the reception quality, to be secured separably to a housing using a tubular magnet holder.

FIG. 2 shows an attachment 1 for improving the reception quality, having a tubular magnet holder 2 which is connected to the holding element 8 by means of the retaining plates 3, 3' of a non-magnetizable material. The tubular magnet holder 2 likewise has through bores 5. Situated on the magnet holder 2 are corresponding magnets 4, 4' with tinned copper foil 13, with their south pole side directed inward. In this exemplary embodiment the magnets (4, 4') are attached on the outside. All that is visible in this illustration is the outer copper foil 13 of the north pole side (7 in FIG. 1). The magnets (4, 4', similar to FIG. 1) have copper foil stuck onto both sides, and are stuck onto the holder 2. Attachment 1 can be secured separably to a housing 10 by means of the holding element 8, as depicted in FIG. 4b.

Figure 3:
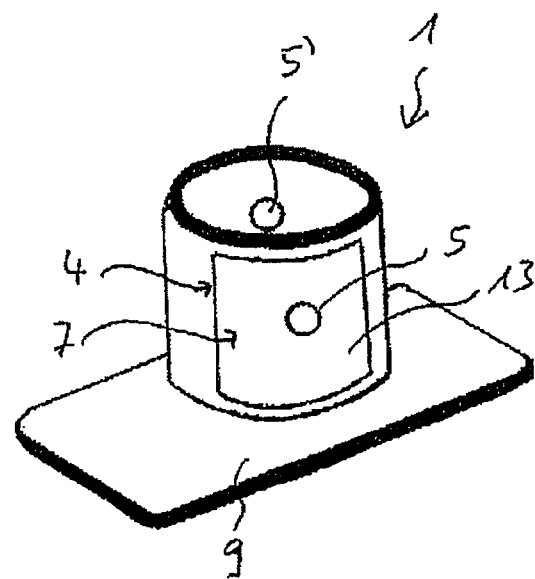
FIG. 3 a perspective view of an attachment for improving the reception quality, having a tubular magnet holder for fixed connection to a housing, and FIGS. 4A-4D two different housing forms (FIGS. 4A, 4B and FIGS. 4C, 4D, respectively), having attachments attached to them for improving the reception quality, and FIGS. 5A-5B a perspective view (FIG. 5A) of a retaining plate as a magnet holder with a magnet glued on and a sectional view (FIG. 5B).

FIG. 3 shows the attachment for improving the reception quality, having a tubular magnet holder 2 which is attachable to a side wall 15 of a housing (see FIG. 4d). To this end, the magnet holder 2 is stuck onto the plate 9, which can be screwed to the housing and with the plate 9 forms the side wall 15.

Figure 4A:
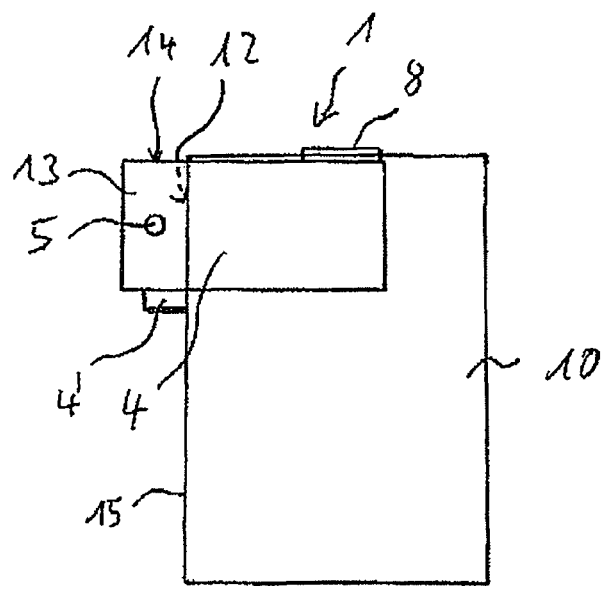
Figure 4B:
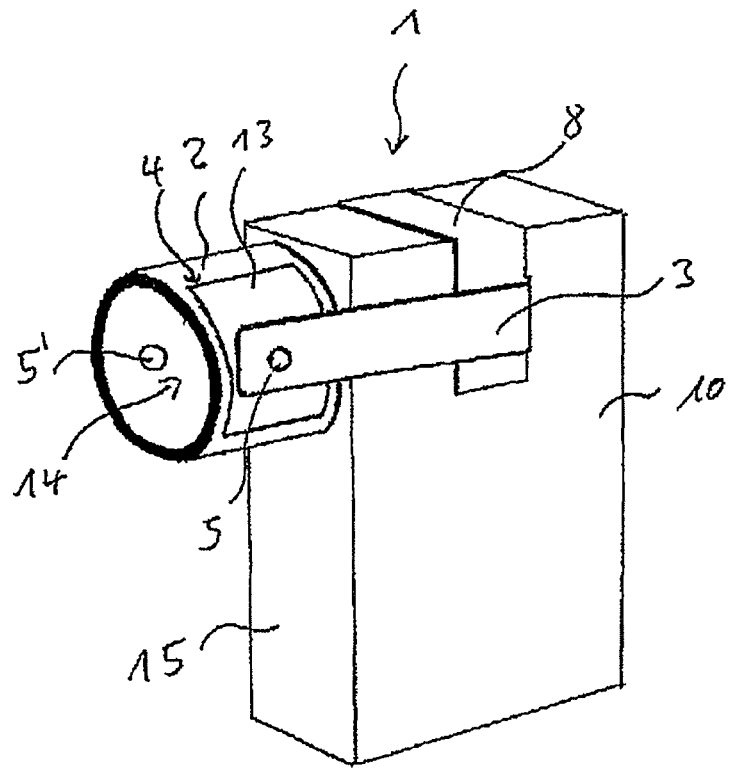
Figure 4C:
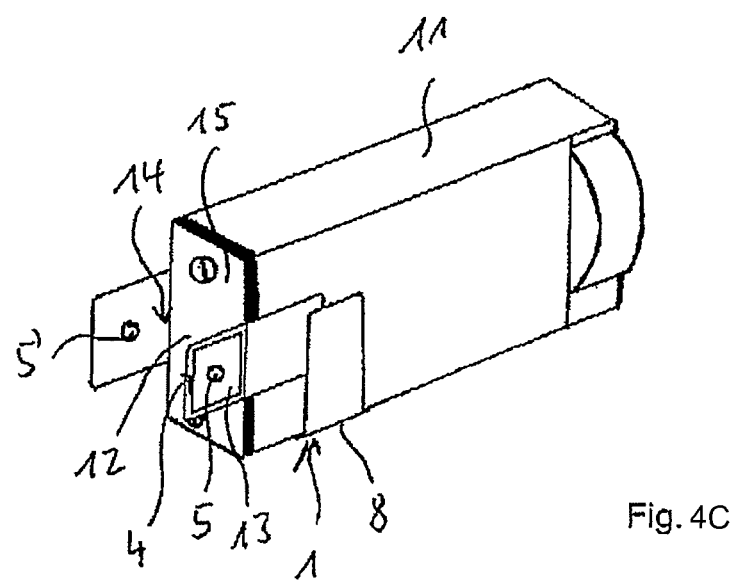

FIGS. 4A through 4D show various rectangular housings 10, 11 of material detector devices, with attachments 1 for improving the reception quality attached to them in front of the antenna surface 12. FIGS. 4A and 4B each show the same housing 10 with attachment 1 according to FIG. 1 and FIG. 2. FIGS. 4C and 4D depict a different housing 11, in which an attachment for improving the reception quality having a magnet holder 2 according to FIGS. 5A and 5B is shown in FIGS. 4C, and in FIG. 4D with an attachment 1 according to FIG. 3. The attachment 1 in FIG. 4C has the magnet holder 2 with the retaining plates 3, 3' of non-magnetizable material, on which the magnets 4, 4' with the tinned copper foil 13 are stuck onto the outside. In FIGS. 4A through 4D the magnets 4, 4' form a magnetic field space 14 directly in front of the antenna surface 12 on the side wall 15.

In principle, it is also possible to fasten the separable attachments for improving the reception quality to the relevant housings 10, 11 by means of Velcro strips over the retaining plates 3, 3' or the magnets 4, 4' instead of the holding element 8, as described in connection with FIG. 1.

The essential thing is that the magnetic field space 14 indicated in FIGS. 1 through 4 is formed between the magnets 4, 4' with the tinned copper foil 13, or instead of it with an oxidized aluminum foil, on every pole side 6, 6', 7, 7' in front of the antenna surface 12 of every housing 10, 11. Optimal results can be achieved with a magnetic field space which extends over a length of at least 15.5 mm beginning at the antenna surface 12 and extending away from it perpendicularly.

In the exemplary embodiments, the magnets 4, 4' are arranged so that the south pole surfaces 6, 6' face toward each other. This is based on the fact that these attachments are matched to a material detector device which is designed and manufactured according to the patent named at the beginning. The material detector device has an antenna structure which makes it necessary to arrange the south pole surfaces 6, 6' as indicated in the exemplary embodiments. According to the named patent, the material detector device could also be provided with an antenna of a different design, so that an attachment 1 according to the patent with north pole surfaces 7, 7' facing each other in the appropriate design would result in an improvement of the reception quality. Of course, a material detector device such as was assumed in the exemplary embodiments is more efficient than a material detector device with a differently designed antenna, in which the attachment 1 would result in an improvement of the reception quality. Thus a material detector device with the attachment 1 for improving the reception quality according to the exemplary embodiments is also more efficient overall.

The attachment for improving the reception quality designed according to the invention achieves the result that the signals which are sensed in particular acoustically are sharper, that is, the differences are more clearly audible, and interference in the known material detector devices cited at the beginning is avoided.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. An attachment for a material detector device having a search antenna polarization instrument, where the material detector device has a housing with an antenna surface assigned to a detection direction, wherein two magnets positioned opposite each other with like poles facing each other whose pole surfaces are covered by a tinned copper or oxidized aluminum layer, where the magnets and the copper or aluminum layer have at least one through bore and the magnets can be or are positioned on the housing of the material detector device so that they extend perpendicular to the antenna surface and form a magnetic field space located between the magnets in front of the antenna surface.

2. The attachment according to claim 1, wherein the at least one through bore is centered with respect to the magnetic field space.

3. The attachment according to claim 1, wherein the copper or aluminum layer has a width of at least 15.5 mm perpendicular to the antenna surface.

4. The attachment according to claim 1, wherein a magnet holder having a retaining plate for each magnet, which extends perpendicular to the antenna surface, is made of a non-magnetizable material and accommodates the magnet outside and/or inside.

5. The attachment according to claim 1, wherein a magnet holder which is in the form of a pipe and accommodates the magnets outside and/or inside.

6. The attachment according to claim 4, wherein the magnet holder may be secured to the housing separably by means of a holding element.

7. The attachment according to claim 4, wherein the attachment is firmly secured to the housing.

8. A material detector device having a search antenna polarization instrument, where the material detector device has a housing with an antenna surface assigned to a detection direction, wherein an attachment having two magnets positioned opposite each other with like poles facing each other whose pole surfaces are covered by a tinned copper or oxidized aluminum layer, where the magnets and the copper or aluminum layer have at least one through bore and the magnets can be or positioned on the housing of the material detector device so that they extend perpendicular to the antenna surface and form a magnetic field space located between the magnets in front of the antenna surface.

9. The material detector device according to claim 8, wherein the at least one through bore is centered with respect to the magnetic field space.

10. The material detector device according to claim 8, wherein the copper or aluminum layer has a width of at least 15.5 mm perpendicular to the antenna surface.

11. The material detector device according to claim 8, wherein a magnet holder having a retaining plate for each magnet, which extends perpendicular to the antenna surface, is made of a non-magnetizable material and accommodates the magnet outside and/or inside.

12. The material detector device according to claim 8, wherein a magnet holder which is in the form of a pipe and accommodates the magnets outside and/or inside.

13. The material detector device according to claim 11, wherein the magnet holder may be secured to the housing separably by means of a holding element.

14. The material detector device according to claim 11, wherein the attachment is firmly secured to the housing.

* * * * *